US012150774B1

(12) United States Patent
Patanaik et al.

(10) Patent No.: US 12,150,774 B1
(45) Date of Patent: Nov. 26, 2024

(54) COMPUTER-IMPLEMENTED SYSTEM FOR DIAGNOSING SLEEP DISORDERS AND A METHOD THEREOF

(71) Applicant: Neurobit Inc., New York, NY (US)

(72) Inventors: Amiya Patanaik, Singapore (SG); Kishan, Singapore (SG); Ankit Brijwasi, Haldwani (IN); Navdeep Mishra, Haldwani (IN)

( * ) Notice: Subject to any disclaimer, the term of this patent is extended or adjusted under 35 U.S.C. 154(b) by 0 days.

(21) Appl. No.: 18/597,993

(22) Filed: Mar. 7, 2024

(51) Int. Cl.
| | |
|---|---|
| *A61B 5/00* | (2006.01) |
| *A61B 5/0205* | (2006.01) |
| *G16H 40/67* | (2018.01) |
| *G16H 50/20* | (2018.01) |
| *H04L 9/32* | (2006.01) |

(52) U.S. Cl.
CPC .......... *A61B 5/4815* (2013.01); *A61B 5/0022* (2013.01); *A61B 5/0205* (2013.01); *A61B 5/7267* (2013.01); *A61B 5/742* (2013.01); *G16H 40/67* (2018.01); *G16H 50/20* (2018.01); *H04L 9/3242* (2013.01); *A61B 2560/0475* (2013.01)

(58) Field of Classification Search
CPC ... A61B 5/4815; A61B 5/0022; A61B 5/0205; A61B 5/7267; A61B 5/742; A61B 2560/0475; G16H 40/67; G16H 50/20; H04L 9/3242
See application file for complete search history.

(56) References Cited

U.S. PATENT DOCUMENTS

| | | |
|---|---|---|
| 2016/0113567 A1 | 4/2016 | Osvath et al. |
| 2020/0138366 A1 | 5/2020 | Low |
| 2021/0045675 A1 | 2/2021 | Lee et al. |

FOREIGN PATENT DOCUMENTS

KR 102371443 B1 3/2022

OTHER PUBLICATIONS

Roxana Tiron et.al, Screening for obstructive sleep apnea with novel hybrid acoustic smartphone app technology, 2020 Journal of Thoracic Disease, Aug. 2020.

*Primary Examiner* — Scott M. Getzow

(57) ABSTRACT

A computer-implemented system for diagnosing sleep disorders is disclosed. The computer-implemented system includes a polysomnography recording device for interfacing with a patient to record a sleep data, a sleep score analysis module configured as a series of analytical blocks for automatically processing a data format, an evaluation module reviews and edits the sleep score for quality control by a physician, a scanning module scans the record of the sleep score within a repository, a montage specification module stores the plurality of montage specifications, a tokenization module grants a pre-determined a plurality of distributed credits in at least one of the analytical blocks, allows a key-based authentication for offline setting, sign the license via an asymmetric key cryptography, a container format module handles physiological sleep data, and includes a signature, a header, and a payload, an authentication module protects a plurality of machine learning models by using a symmetric encryption method.

20 Claims, 11 Drawing Sheets

COMPUTER-IMPLEMENTED SYSTEM FOR DIAGNOSING SLEEP DISORDERS AND A METHOD THEREOF

FIELD OF INVENTION

Embodiments of a present disclosure relate to the field of diagnostic and more particularly to a computer-implemented system for diagnosing sleep disorders and a method thereof.

BACKGROUND

Sleep is a naturally recurring state of altered consciousness and reduced responsiveness to external stimuli that is essential for the well-being and functioning of the human body. It is a complex and dynamic process that involves different stages and cycles. Sleep plays a crucial role in maintaining overall neurological health, and disturbances in sleep patterns can significantly impact various neurological disorders. Inadequate sleep or improper sleep may cause various neurological disorders such as Epilepsy, Alzheimer's Disease, Parkinson's Disease, Multiple Sclerosis (MS), Migraines, Headaches, Stroke, and the like. Accordingly, measurement of quality and quantity of sleep is important for preventing and/or correcting sleep disorders.

A polysomnography (PSG) is universally recognized as a standard for sleep measurement. The specific channels such as eye movement, leg movement, and the like recorded may vary based on the measurement settings in PSG. In a controlled clinical environment, where a physician is present, it's common to record data from all available channels. This is often referred to as a level-1 sleep study. Conversely, in a home-based setting, the focus might be limited to only the respiration or oximeter channels depending on this specific channels are recorded. The intricate process of capturing these signals involves a specialized recording device that digitally captures these physiological signals. The recorder interfaces with a workstation for the storage and subsequent analysis of the data. Typically, the raw data acquired is stored in the universally accepted European Data Format (EDF), ensuring interoperability and ease of access.

The critical task of interpreting wealth of data falls upon a specially trained physician, often a Registered Polysomnographic Technologist (RPSGT). This expert meticulously combs through the data in manageable segments, ranging from 30 seconds to 5 minutes. Adhering to established guidelines, such as the American Academy of Sleep Medicine (AASM) Manual for the scoring of Sleep and associated events, the technician analyses the data.

However, this manual process of scoring of sleep is fraught with challenges. It is not only time-consuming and labour-intensive but also introduces significant variability and potential bias across different raters. The reliance on human judgment, despite adherence to standardized guidelines, can lead to inconsistencies in scoring, especially when considering the nuanced nature of sleep patterns and associated events. Moreover, the process is expensive, requiring specialized training and expertise, which may not be readily available in all clinical settings.

Hence, there is a need of a computer-implemented system for diagnosing sleep disorders and a method thereof which addresses the aforementioned issues.

OBJECTIVE OF THE INVENTION

An objective of the present invention is to provide an automatic computer implemented system for diagnosing sleep disorders.

Another objective of the present invention is to provide a time-efficient system by avoiding manual labour, variability, and potential bias across different raters.

Yet, an objective of the present invention is to provide a cost-effective system as it does not require specialized training and expertise, which may not be readily available in all clinical settings.

BRIEF DESCRIPTION

In accordance with one embodiment of the disclosure a computer-implemented system for diagnosing sleep disorders is provided. The computer-implemented system includes a hardware processor, a polysomnography recording device, and a memory. The polysomnography recording device interfaces with a patient to record a sleep data. The sleep data comprises at least one of an eye motion, a muscle activity, respiratory patterns, blood oxygen saturation, heart rhythms, and blood flow. The memory is coupled to the hardware processor and the polysomnography recording device. The memory includes a set of instructions in the form of a processing subsystem, configured to be executed by the hardware processor. The processing subsystem is hosted on a server and configured to execute on a network to control bidirectional communications among a plurality of modules. The plurality of modules includes a sleep score analysis module, an evaluation module, a scanning module, a montage specification module, a tokenization module, a container format module, and an authentication module. The sleep score analysis module is configured as a series of analytical blocks for automatically processing a data format to produce a standardized format of a sleep score. The sleep score analysis module uses the license and a plurality of montage specifications. The evaluation module is operatively connected to the sleep score analysis module and configured to review and edit the sleep score for quality control by a physician. The scanning module is operatively connected to the sleep score analysis module and configured to scan the record of the sleep score within a repository on a workstation to extract names of a plurality of channels and display the extracted channels to the physician. The plurality of channels comprises a plurality of signals generated from physical part of a patient. The scanning module enables the physician to align the plurality of channels with corresponding channel names present in recordings. The scanning module enables the physician to input a criteria for an automated scoring process and detect a sleep disorder. The criteria comprises a format for saving a sleep score, a predetermined demographic details, and a plurality of guidelines required for sleep scoring. The montage specification module operatively coupled to the scanning module and the sleep score analysis module, wherein the montage specification module is configured to store the plurality of montage specifications as a predefined notation dictionary. The tokenization module is operatively connected with the montage specification module. The tokenization module is configured to grant a pre-determined a plurality of distributed credits in at least one of the analytical blocks, to a user. Each block of credit includes an expiration date provide a plurality of scoring methods for providing an analysis service, each service is designed for a specific scoring aspect and a predefined types of recordings. The tokenization module is also configured to associate the analysis service with a cost multiplier. The analysis service is disabled by assigning a negative cost multiplier. Further, the tokenization module is configured to register the tokenization as a tokenization license including a credit block, the expiration date, a license type, and the cost multiplier table. The tokenization license is stored in a cryptographic storage device connected directly to the workstation or on a cloud authentication server. Furthermore, the tokenization module is configured to allow a key-based authentication for offline setting and enforce the tokenization in an offline setting, the tokenization licenses and a credit accounting and are carried out in a hardware security module with a real-time clock and a unique identifier. Furthermore, the tokenization module is configured to sign the license and a communication between the sleep scoring analysis via an asymmetric key cryptography on the workstation and the cloud authentication server. Furthermore, the tokenization module is configured to update the license using over-the-air mechanism, wherein the updating is irrespective of the workstation connection with Internet. The container format module is operatively connected with the tokenization module and configured for handling physiological sleep data. A container format comprises a signature, a header, and a payload. The signature includes a predetermined bytes to inform an operating system about the container format and a byte indicating payload compression. The header is of fixed length and carries a string representing a dictionary that includes version, revision, record duration, start date and time for the recording, unique identifier, and a plurality of field listing keys. The plurality of field listing keys is defined in a header present in payload. The authentication module is operatively connected with montage specification module. The authentication module is configured to protect a plurality of machine learning models by using a symmetric encryption method. The authentication module is also configured to compile a code into machine code to protect a source code. Further, the authentication module is configured to serialize the plurality of machine learning models, encrypt the plurality of machine learning models using a key and deploy into an analytics application. The analytics application requests an encryption key to decrypt and deserialize the machine learning models for performing analysis.

In accordance with another embodiment a method for analyzing sleep for diagnosing sleep disorder is provided. The method includes interfacing, by a polysomnography recording device, with a patient to record a sleep data wherein the sleep data comprises at least one of an eye motion, a muscle activity, respiratory patterns, blood oxygen saturation, heart rhythms, and blood flow. The method also includes automatically processing, by a sleep score analysis module of a processing subsystem, a data format to produce a standardized format of a sleep score, wherein the sleep score analysis module uses the license and a plurality of montage specifications. Further, the method includes reviewing and editing, by an evaluation module of the processing subsystem, the sleep score for quality control by a physician. scanning, by a scanning module of the processing subsystem, the record of the sleep score within a repository on a workstation to extract names of a plurality of channels and display the extracted channels to the physician, wherein the plurality of channels comprises a plurality of signals generated from physical part of a patient. Furthermore, the method includes enabling, by the scanning module of the processing subsystem, the physician to align the plurality of channels with corresponding channel names present in recordings. Moreover, the method includes enabling, by the scanning module of the processing subsystem, the physician to input a criteria for an automated scoring process, wherein the criteria comprises a format for saving a sleep score, a predetermined demographic details, and a plurality of guidelines required for sleep scoring.

Furthermore, the method includes storing, by a montage specification module of the processing subsystem, the plurality of montage specifications as a predefined notation dictionary. Furthermore, the method includes granting, by a tokenization module of the processing subsystem, a predetermined a plurality of distributed credits in at least one of the analytical blocks, to a user, wherein each block of credit includes an expiration date. Furthermore, the method includes providing, by tokenization module of the processing subsystem, a plurality of scoring methods for providing an analysis service, each service is designed for a specific scoring aspect and a predefined types of recordings. Furthermore, the method includes associating, by tokenization module of the processing subsystem, the analysis service with a cost multiplier, wherein the analysis service is disabled by assigning a negative cost multiplier. Furthermore, the method includes registering, by tokenization module of the processing subsystem, the tokenization as a tokenization license comprising a credit block, the expiration date, a license type, and the cost multiplier table. The tokenization license is stored in a cryptographic storage device connected directly to the workstation or on a cloud authentication server. Furthermore, the method includes allowing, by tokenization module of the processing subsystem, a key-based authentication for offline setting and enforce the tokenization in an offline setting, the tokenization licenses and a credit accounting and are carried out in a hardware security module with a real-time clock and a unique identifier. Furthermore, the method includes signing, by tokenization module of the processing subsystem, the license, and a communication between the sleep scoring analysis via an asymmetric key cryptography on the workstation and the cloud authentication server. Furthermore, the method includes updating, by tokenization module of the processing subsystem, the license using over-the-air mechanism, wherein the updating is irrespective of the workstation connection with Internet. Furthermore, the method includes handling, by a container format module of the processing subsystem, physiological sleep data, wherein a container format comprises a signature, a header, and a payload. Furthermore, the method includes providing, by the container format module of the processing subsystem, a predetermined bytes to inform an operating system about the container format and a byte indicating payload compression. Furthermore, the method includes carrying, by the header of the by the container format module of the processing subsystem, a string representing a dictionary that includes version, revision, record duration, start date and time for the recording, unique identifier, and a plurality of field listing keys, wherein, the plurality of field listing keys is defined in header is present in payload. Furthermore, the method includes protecting, by an authentication module of the processing subsystem, a plurality of machine learning models by using a symmetric encryption method. Furthermore, the method includes compiling, by the authentication module of the processing subsystem, a code into machine code to protect a source code. Furthermore, the method includes serializing, by the authentication module of the processing subsystem, the plurality of machine learning models, encrypt the plurality of machine learning models using a key and deploy into an analytics application, wherein the analytics application requests an encryption key to decrypt and deserialize the machine learning models for performing analysis.

In accordance with an embodiment of the present disclosure a non-transitory computer-readable medium storing a computer program that, when executed by a processor, causes the processor to a method for analyzing sleep for diagnosing sleep disorder is provided. The method includes interfacing, by a polysomnography recording device, with a patient to record a sleep data wherein the sleep data comprises at least one of an eye motion, a muscle activity, respiratory patterns, blood oxygen saturation, heart rhythms, and blood flow. The method also includes automatically processing, by a sleep score analysis module of a processing subsystem, a data format to produce a standardized format of a sleep score, wherein the sleep score analysis module uses the license and a plurality of montage specifications. Further, the method includes reviewing and editing, by an evaluation module of the processing subsystem, the sleep score for quality control by a physician. scanning, by a scanning module of the processing subsystem, the record of the sleep score within a repository on a workstation to extract names of a plurality of channels and display the extracted channels to the physician, wherein the plurality of channels comprises a plurality of signals generated from physical part of a patient. Furthermore, the method includes enabling, by the scanning module of the processing subsystem, the physician to align the plurality of channels with corresponding channel names present in recordings. Furthermore, the method includes enabling, by the scanning module of the processing subsystem, the physician to input a criteria for an automated scoring process, wherein the criteria comprises a format for saving a sleep score, a predetermined demographic details, and a plurality of guidelines required for sleep scoring. Furthermore, the method includes storing, by a montage specification module of the processing subsystem, the plurality of montage specifications as a predefined notation dictionary. Furthermore, the method includes granting, by a tokenization module of the processing subsystem, a pre-determined a plurality of distributed credits in at least one of the analytical blocks, to a user, wherein each block of credit includes an expiration date. Furthermore, the method includes providing, by tokenization module of the processing subsystem, a plurality of scoring methods for providing an analysis service, each service is designed for a specific scoring aspect and a predefined types of recordings. Furthermore, the method includes associating, by tokenization module of the processing subsystem, the analysis service with a cost multiplier, wherein the analysis service is disabled by assigning a negative cost multiplier. Furthermore, the method includes registering, by tokenization module of the processing subsystem, the tokenization as a tokenization license comprising a credit block, the expiration date, a license type, and the cost multiplier table, The tokenization license is stored in a cryptographic storage device connected directly to the workstation or on a cloud authentication server. Furthermore, the method includes allowing, by tokenization module of the processing subsystem, a key-based authentication for offline setting and enforce the tokenization in an offline setting, the tokenization licenses and a credit accounting and are carried out in a hardware security module with a real-time clock and a unique identifier. Furthermore, the method includes signing, by tokenization module of the processing subsystem, the license, and a communication between the sleep scoring analysis via an asymmetric key cryptography on the workstation and the cloud authentication server. Furthermore, the method includes updating, by tokenization module of the processing subsystem, the license using over-the-air mechanism, wherein the updating is irrespective of the workstation connection with Internet. Furthermore, the method includes handling, by a container format module of the processing subsystem, physiological sleep data, wherein a container format comprises a signature, a header, and a payload. Furthermore, the method includes providing, by the container format module of the processing subsystem, a predetermined bytes to inform an operating system about the container format and a byte indicating payload compression. Furthermore, the method includes carrying, by the header of the by the container format module of the processing subsystem, a string representing a dictionary that includes version, revision, record duration, start date and time for the recording, unique identifier, and a plurality of field listing keys, wherein, the plurality of field listing keys is defined in header is present in payload. Furthermore, the method includes protecting, by an authentication module of the processing subsystem, a plurality of machine learning models by using a symmetric encryption method. Furthermore, the method includes compiling, by the authentication module of the processing subsystem, a code into machine code to protect a source code. Furthermore, the method includes serializing, by the authentication module of the processing subsystem, the plurality of machine learning models, encrypt the plurality of machine learning models using a key and deploy into an analytics application, wherein the analytics application requests an encryption key to decrypt and deserialize the machine learning models for performing analysis.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Figure 1:
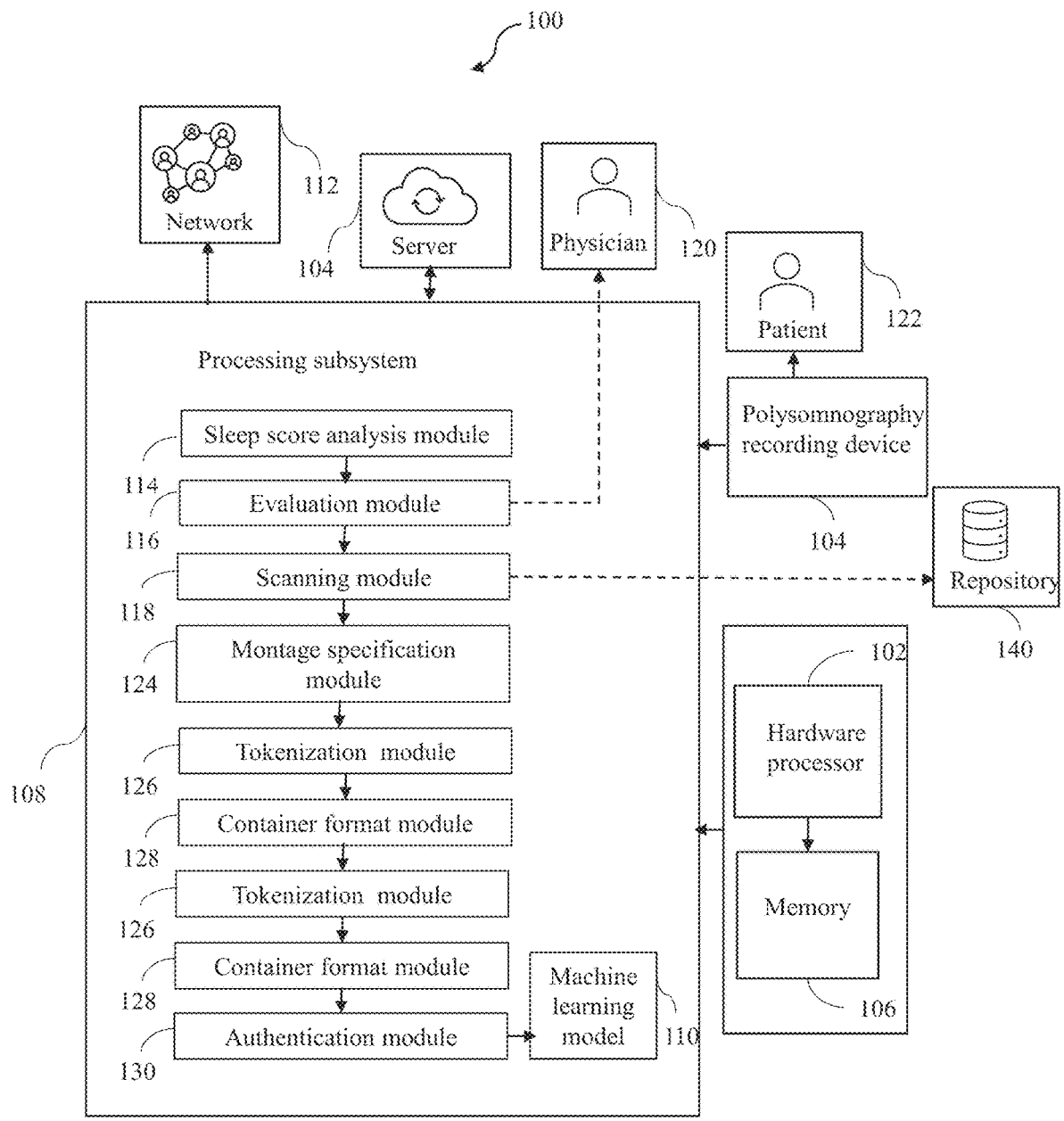
FIG. 1 is a block diagram a computer-implemented system for diagnosing sleep disorders in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures, or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

In the discussion that follows, references are made to a 'first user', 'second user' and a 'third user' with respect to users who verify a plurality of documents across multiple levels. Specifically, the 'first user' and the 'second user' verifies the plurality of documents at a first level and the 'third user' verifies the said plurality of documents at a second level respectively. Further, the 'first user', 'second user' and the 'third user' belong to a single organisation or company.

Embodiments of the present disclosure relate to a computer-implemented system for diagnosing sleep disorders. The computer-implemented system includes a hardware processor, a polysomnography recording device, and a memory. The hardware processor. The polysomnography recording device for interfacing with a patient to record a sleep data. The sleep data comprises at least one of an eye motion, a muscle activity, respiratory patterns, blood oxygen saturation, heart rhythms, and blood flow. The memory coupled to the hardware processor and the polysomnography recording device. The memory includes a set of instructions in the form of a processing subsystem, configured to be executed by the hardware processor. The processing subsystem is hosted on a server and configured to execute on a network to control bidirectional communications among a plurality of modules. The plurality of modules includes a sleep score analysis module, an evaluation module, a scanning module, a montage specification module, a tokenization module, a container format module, and an authentication module. The sleep score analysis module is configured as a series of analytical blocks for automatically processing a data format to produce a standardized format of a sleep score. The sleep score analysis module uses the license and a plurality of montage specifications. The evaluation module is operatively connected to the sleep score analysis module and configured to review and edit the sleep score for quality control by a physician. The scanning module is operatively connected to the sleep score analysis module and configured to scan the record of the sleep score and store within a repository on a workstation to extract names of a plurality of channels and display the extracted channels to the physician. The plurality of channels comprises a plurality of signals generated from physical part of a patient. The scanning module enables the physician to align the plurality of channels with corresponding channel names present in recordings. The scanning module enables the physician to input a criteria for an automated scoring process, wherein the criteria comprises a format for saving a sleep score, a predetermined demographic details, and a plurality of guidelines required for sleep scoring. The montage specification module operatively coupled to the scanning module and the sleep score analysis module, wherein the montage specification module is configured to store the plurality of montage specifications as a predefined notation dictionary. The tokenization module is operatively connected with the montage specification module. The tokenization module is configured to grant a pre-determined a plurality of distributed credits in at least one of the analytical blocks, to a user. Each block of credit includes an expiration date provide a plurality of scoring methods for providing an analysis service, each service is designed for a specific scoring aspect and a predefined types of recordings. The tokenization module is also configured to associate the analysis service with a cost multiplier. The analysis service is disabled by assigning a negative cost multiplier. Further, the tokenization module is configured to register the tokenization as a tokenization license including a credit block, the expiration date, a license type, and the cost multiplier table. The tokenization license is stored in a cryptographic storage device connected directly to the workstation or on a cloud authentication server. Furthermore, the tokenization module is configured to allow a key-based authentication for offline setting and enforce the tokenization in an offline setting, the tokenization licenses and a credit accounting and are carried out in a hardware security module with a real-time clock and a unique identifier. Furthermore, the tokenization module is configured to sign the license and a communication between the sleep scoring analysis via an asymmetric key cryptography on the workstation and the cloud authentication server. Furthermore, the tokenization module is configured to update the license using over-the-air mechanism, wherein the updating is irrespective of the workstation connection with Internet. The container format module operatively connected with the tokenization module and configured for handling physiological sleep data. A container format comprises a signature, a header, and a payload. The signature includes a predetermined bytes to inform an operating system about the container format and a byte indicating payload compression. The header is of fixed length and carries a string representing a dictionary that includes version, revision, record duration, start date and time for the recording, unique identifier, and a plurality of field listing keys. The plurality of field listing keys is defined in header is present in payload. The authentication module operatively connected with montage specification module. The authentication module is configured to protect a plurality of machine learning models by using a symmetric encryption method. The authentication module is also configured to compile a code into machine code to protect a source code. Further, the authentication module is configured to serialize the plurality of machine learning models, encrypt the plurality of machine learning models using a key and deploy into an analytics application. The analytics application requests an encryption key to decrypt and deserialize the machine learning models for performing analysis.

FIG. 1 is a block diagram representing a computer-implemented system 100 for diagnosing sleep disorders including in accordance with an embodiment of the present disclosure. The computer-implemented system 100 includes a hardware processor 102, a polysomnography recording device 104, a memory 106. The polysomnography recording device 104 is configured to interface with a patient 122 to record a sleep data. The sleep data includes at least one of an eye motion, a muscle activity, respiratory patterns, blood oxygen saturation, heart rhythms, and blood flow. The memory 106 coupled to the hardware processor 102 and the polysomnography recording device 104. The memory 106 includes a set of instructions in the form of a processing subsystem 108, configured to be executed by the hardware processor 102. The processing subsystem 108 is hosted on a server 110 and configured to execute on a network 112 to control bidirectional communications among a plurality of modules. In one embodiment, the server 104 may include a cloud server. In another embodiment, the server 104 may include a local server. In one embodiment, the network 106 may include a wired network such as a local area network (LAN). In another embodiment, the network may include a wireless network such as Wi-Fi, Bluetooth, Zigbee, near-field communication (NFC), infrared communication (RFID), or the like.

The plurality of modules includes a sleep score analysis module 114, an evaluation module 116, a scanning module 118, a montage specification module 124, a tokenization module 126, a container format module 128, and an authentication module 130.

The sleep score analysis module 114 is configured as a series of analytical blocks for automatically processing a data format to produce a standardized format of a sleep score. The sleep score analysis module 114 uses the license and a plurality of montage specifications.

The evaluation module 116 is operatively connected to the sleep score analysis module 114 and is configured to review and edit the sleep score for quality control by a physician 120.

The scanning module 118 is operatively connected to the sleep score analysis module 114 and configured to scan the record of the sleep score and store within a repository 140 on a workstation to extract names of a plurality of channels and display the extracted channels to the physician 120. The plurality of channels comprises a plurality of signals generated from physical part of a patient 122.

The scanning module 118 is configured to enable the physician 120 to align the plurality of channels with corresponding channel names present in recordings. The scanning module 118 is also configured to enable the physician 120 to input a criteria for an automated scoring process. The criteria includes a format for saving a sleep score, a predetermined demographic details, and a plurality of guidelines required for sleep scoring.

The montage specification module 124 is operatively coupled to the scanning module and the sleep score analysis module 114. The montage specification module 124 is configured to store the plurality of montage specifications as a predefined notation dictionary.

The tokenization module 126 is operatively connected with the montage specification module 126. The tokenization module 126 is configured to grant a pre-determined a plurality of distributed credits in at least one of the analytical blocks, to a user, each block of credit comprises an expiration date. The tokenization module 126 is also configured to provide a plurality of scoring methods for providing an analysis service, each service is designed for a specific scoring aspect and a predefined types of recordings. Further, the tokenization module 126 is configured to associate the analysis service with a cost multiplier, wherein the analysis service is disabled by assigning a negative cost multiplier. Furthermore, the tokenization module 126 is configured to register the tokenization as a tokenization license including a credit block, the expiration date, a license type, and the cost multiplier table. The tokenization license is stored in a cryptographic storage device connected directly to the workstation or on a cloud authentication server. Furthermore, the tokenization module 126 is configured to allow a key-based authentication for offline setting and enforce the tokenization in an offline setting, the tokenization licenses and a credit accounting and are carried out in a hardware security module with a real-time clock and a unique identifier. Furthermore, the tokenization module 126 is configured to sign the license and a communication between the sleep scoring analysis module via an asymmetric key cryptography on the workstation and the cloud authentication server. Furthermore, the tokenization module 126 is configured to update the license using over-the-air mechanism, wherein the updating is irrespective of the workstation connection with Internet.

The container format module 128 is operatively connected with the tokenization module 126 and configured for handling physiological sleep data, wherein a container format 128 comprises a signature, a header, and a payload. The signature includes a predetermined bytes to inform an operating system about the container format and a byte indicating payload compression. The header is of fixed length and carries a string representing a dictionary that includes version, revision, record duration, start date and time for the recording, unique identifier, and a plurality of field listing keys, wherein, the plurality of field listing keys is defined in header is present in payload.

The authentication module 130 is operatively connected with montage specification module 124. The authentication module 130 is configured to protect a plurality of machine learning models by using a symmetric encryption method. The authentication module 130 is configured to compile a code into machine code to protect a source code. Further, the authentication module 130 is configured to serialize the plurality of machine learning models, encrypt the plurality of machine learning models using a key and deploy into an analytics application. The analytics application requests an encryption key to decrypt and deserialize the machine learning models for performing analysis.

Figure 2:
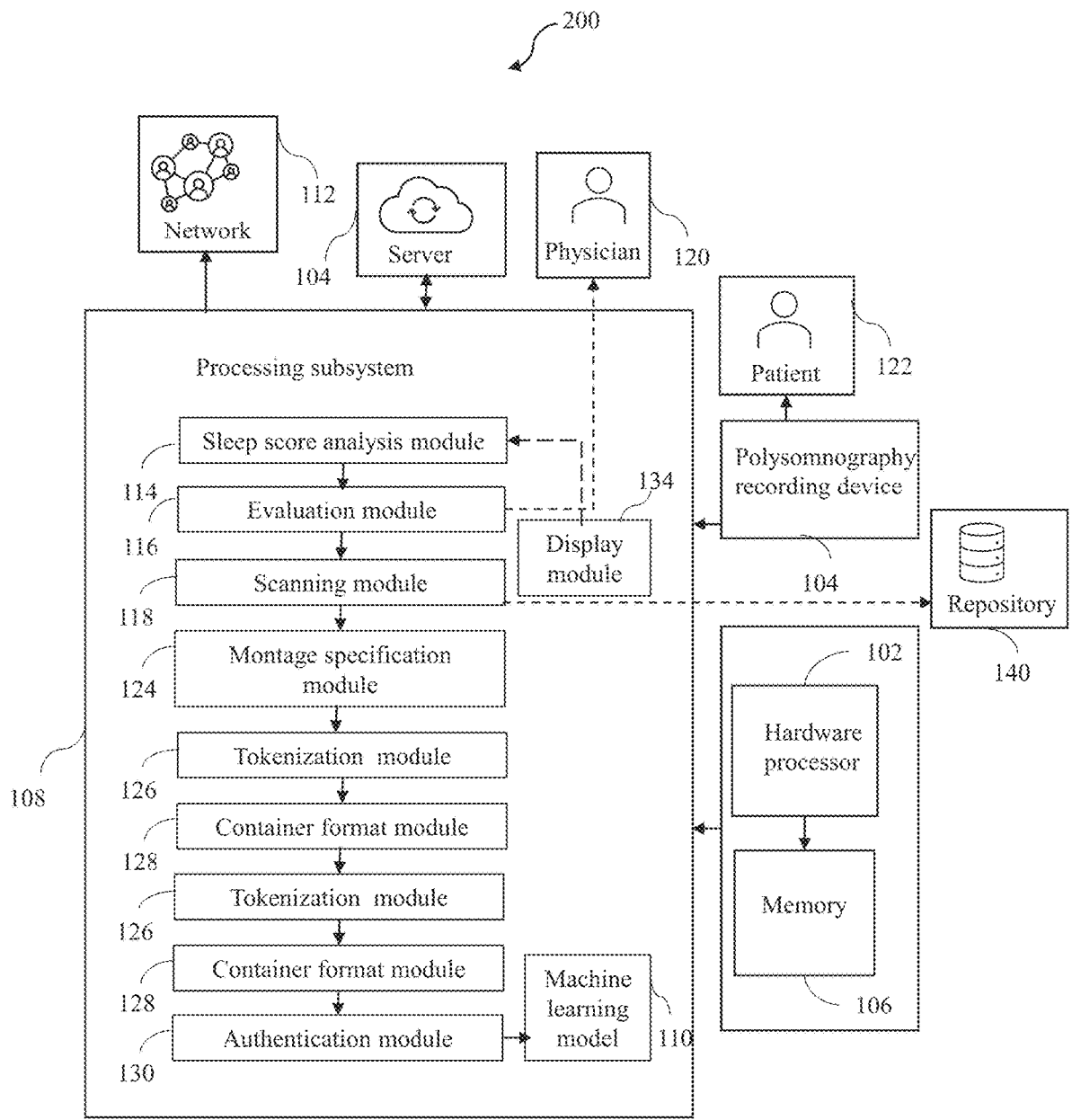
FIG. 2 is a block diagram an exemplary embodiment for the computer-implemented system for diagnosing sleep disorders of FIG. 1 in accordance with an embodiment of the present disclosure.

FIG. 2 is a block diagram an exemplary embodiment for the computer-implemented system 100 for diagnosing sleep disorders of FIG. 1 in accordance with an embodiment of the present disclosure. The computer-implemented system includes a display module 134 operatively coupled to a sleep score analysis module 114. The display module 134 is configured to display a report related to the sleep score upon analysing the sleep data and integrates the report with an electronic recording unit to forward the report to a physician 120.

Considering a non-limiting example where a patient X wants to record the sleep data by using a recording device such as a polysomnography recording device. The polysomnography recording device 104 interfaces with the patient X to record the sleep data. The sleep data includes an eye motion, a muscle activity, respiratory patterns, blood oxygen saturation, heart rhythms, blood flow, and the like. The sleep score analysis module 114 analyses the recorded data stored in the memory in the form of analytical blocks for automatically processing the data to produce a standardized format of the sleep score. In one embodiment, the scoring methods for analysis is designed for a specific scoring aspect and a predefined types of recordings. The stored data is analyzed by using license and montage specifications. In one embodiment, the montages represents organized collection of channels. In one embodiment, the channels are the signals sent by the patient X body parts such as heart rate, blood pressure, and the like. In one embodiment, the license encompasses the allocated credit blocks, their expiration dates, license types which may impose legal usage restriction. The recorded sleep score is scanned by the scanning module 118 and stored within a repository 140 on a workstation to extract names of the plurality of channels and display the extracted channels to the physician 120. In one embodiment, the scanning module 118 enables the physician 120 to input a criteria for an automated scoring process detect a sleep disorder. The criteria comprises a format for saving a sleep score, a predetermined demographic details, and a plurality of guidelines required for sleep scoring. After analysis of the sleep score, the computer-implemented system enables the use to review the sleep score by the physician for diagnosis of the neurological disease. Also, based on patient's history the physician 120 is able to edit the sleep score for future diagnosis.

The stored data is authenticated by the authentication module 130 via a key-based authentication for offline setting and enforce the tokenization in an offline setting, the tokenization licenses and a credit accounting and are carried out in a hardware security module with a real-time clock and a unique identifier. In one embodiment, the authentication module 130 protects a plurality of machine learning models by using a symmetric encryption method. The authentication is data sign the license and a communication between the sleep scoring analysis via an asymmetric key cryptography on the workstation and the cloud authentication server. In one embodiment, the license can be updated. In one embodiment, the sleep data is handled by the container format module 128. The sleep data includes physiological sleep data, a signature, a header, and a payload.

Figure 3:
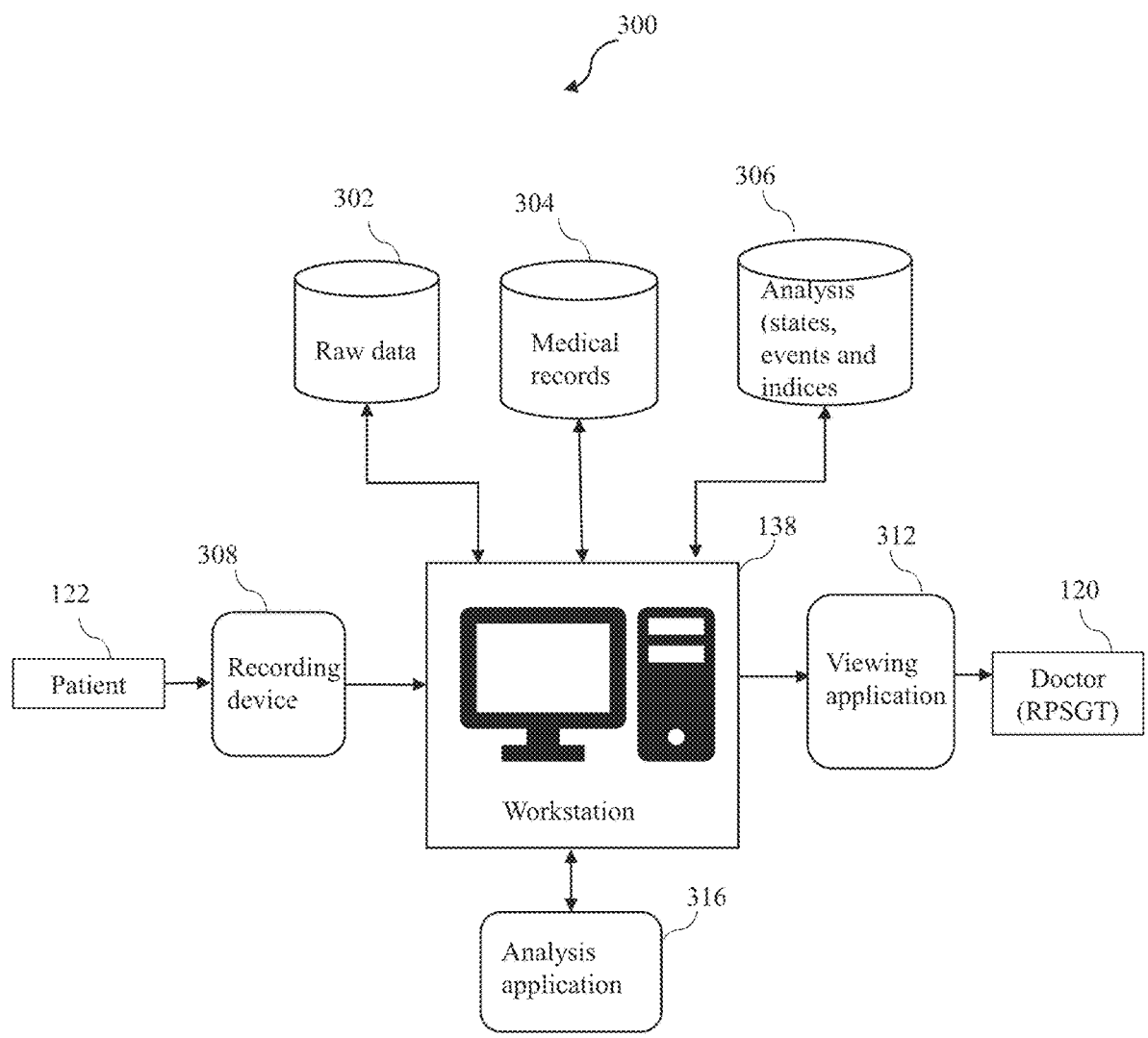
FIG. 3 is a block diagram representing artificial intelligence assisted sleep scoring workflow of FIG. 1 in accordance with an embodiment of the present disclosure.

FIG. 3 is a block diagram representing artificial intelligence assisted sleep scoring workflow of FIG. 1 in accordance with an embodiment of the present disclosure. The patient 122 sleep score is recorded by using a recording device 308. The recorded score is transmitted to the workstation 138. The analysis application 316 is installed in the workstation 138 to analyze the sleep score. A viewing application 312 is also installed on the workstation 138 to view the sleep score. The analysis software interfaces directly with the raw data 302, analyses it and pushes the automatic scores back 306. The workstation 138 receives raw data 302 and data form medical records 304 and other analyzed documents 306. Unlike cloud-based scoring systems, the raw data never leaves the local workstation 138. This significantly reduces the analysis time and eliminates concerns around data security and privacy. These automatic scores can then be viewed in the viewing software 312 by the physician 120. The physician 120 may review and edit the scores for quality control and compile the results to create the detailed report very similar to the non-artificial intelligence (AI) assisted workflow. The report can then be interpreted by the physician 120. The invention therefore introduces minimal changes to the existing workflow of manual scoring. Minimizing disruption to the existing workflow is crucial for several compelling reasons. Established workflows are the culmination of iterative refinements, ensuring that operations run smoothly and efficiently. Introducing sudden changes can lead to confusion, a drop in efficiency, and an increased likelihood of mistakes. Moreover, technicians are trained and are familiar with current procedures. Altering these can necessitate extensive retraining, consuming valuable time and resources. Furthermore, a consistent workflow ensures that service delivery remains uninterrupted, which is essential for maintaining customer trust and satisfaction.

Figure 4:
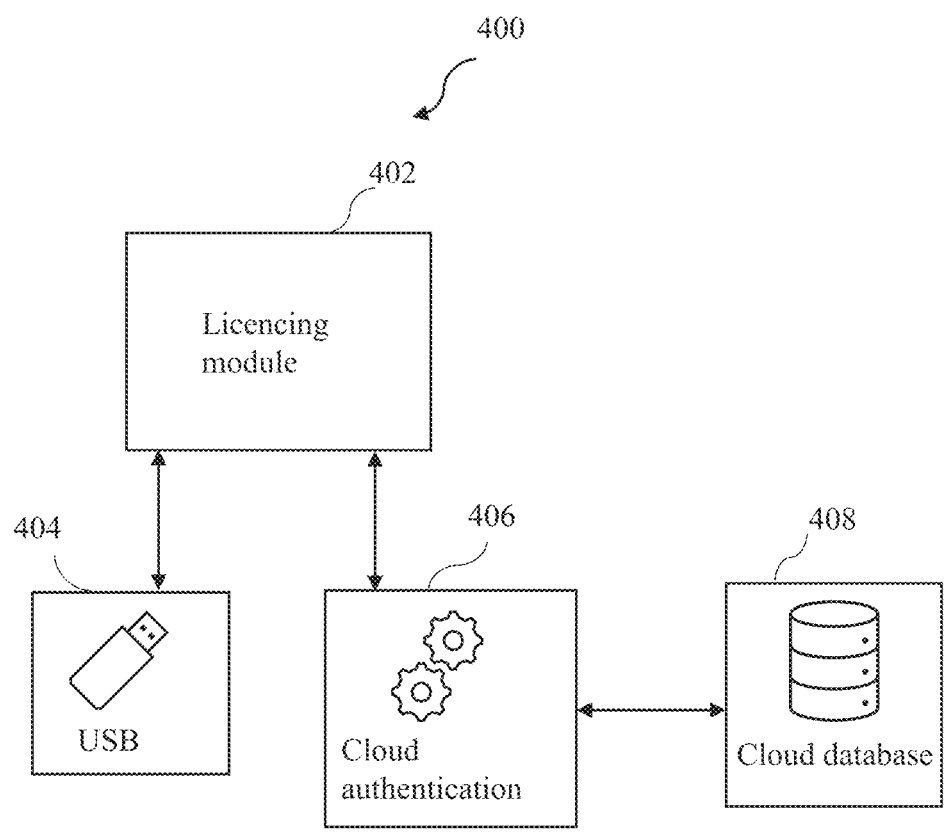
FIG. 4 is a block diagram representing an authentication module of FIG. 1 in accordance with an embodiment of the present disclosure.

FIG. 4 is a block diagram representing an authentication module 130 of FIG. 1 in accordance with an embodiment of the present disclosure. The licensing module 402 is either stored on a hardware security module (HSM) which is directly connected to the workstation 138 or through a cloud authentication server 406. The HSM is implemented in the form of a universal serial bus (USB) dongle 404 with a real-time clock (RTC) to enforce time restriction on the credit blocks. Each HSM is associated with a universally Unique Identifier (UUID). The users are presented with an option to either select a dongle-based authentication or a cloud-based authentication when the analytics application starts. In one embodiment, the cloud-based authentication is performed by logging in to the computer-implemented system, wherein the login is done by the credentials provided to the user by the computer-implemented system. Once a user makes a choice, in the subsequent sessions, the choice is automatically selected by default. The user has the option to log out of a specific authentication mode at any time and revert to the selection menu. Both the authentication methods provide equally high level of data security and privacy as the raw data is directly processed locally in the workstation 138, only the tokenization in the form of access control and credit management is handled through the HSM or through the cloud authentication server. The HSM based authentication is important in high security environments, where strong technical safeguards are required to ensure that data never leaks out of the workstation 138 environment.

Such environments are often air-gapped, that is are disconnected from the internet. The invention discloses methods to manage and update the license with equal ease in both situations. Managing the license over the cloud authentication server is trivial. However, managing the license can be complicated for the HSM based authentication, as the workstation 138 cannot be accessed remotely. Sending a new HSM every time an update is necessary is cumbersome and costly, while physically sending the existing HSM for updates can be slow and disruptive to the workflow. To solve this issue, the invention discloses an over the air (OTA) update method for the HSM. In this method a digitally signed and encrypted license file is sent digitally to the user. The specific method of sending could be e-mail or messaging but is irrelevant to the OTA process. This license can then be imported into the analysis software to update the license. The license file is constructed in a way that it can only be installed on the designated HSM with a given UUID. The cryptographic and security protocols to ensure the enforcement of the tokenization is discussed in later sections.

Figure 5:
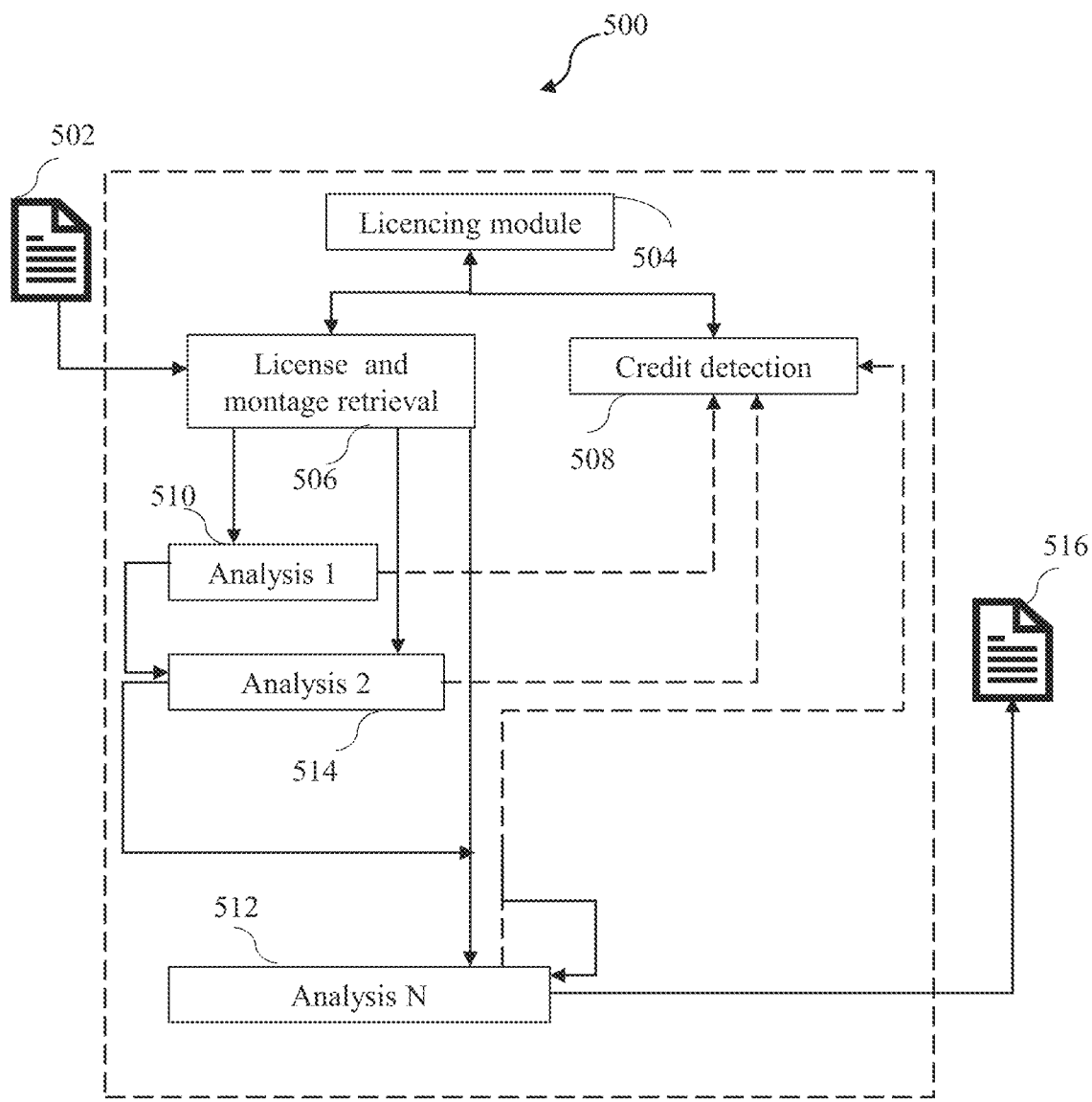
FIG. 5 is a block diagram representing a sleep scoring analysis module of FIG. 1 in accordance with an embodiment of the present disclosure.

FIG. 5 is a block diagram representing a sleep scoring analysis module of FIG. 1 in accordance with an embodiment of the present disclosure. The sleep scoring analysis module includes of a plurality of analysis 510, 514, 512 which are run in series. The order of the analysis is such that any interdependency between the analysis is respected. Each analysis additionally requires the license information to ascertain which services are available to the user and their associated costs. The montage specification is also required to account for any specific additional considerations for the analysis. This is accomplished by a central license and montage retrieval module 506 which directly communicates with the licensing module 402 which implements the tokenization framework. Once the analysis is complete, each analysis module deducts the appropriate credits through a credit deduction module 508 which again communicates with the licensing module 504. Due to the standardized nature of the I/O as well as the tokenization system, extension or new addition of analysis is straightforward. The process involves updating the montage specification and input format specification if new channels or processed data needs to be added. The updating or introducing the appropriate analysis at the right order. In one embodiment, the analytical blocks processes Neurobit Data Format (NDF) 502. In one embodiment, a fixed-length header carrying a string representing a JSON dictionary 516.

Figure 6:
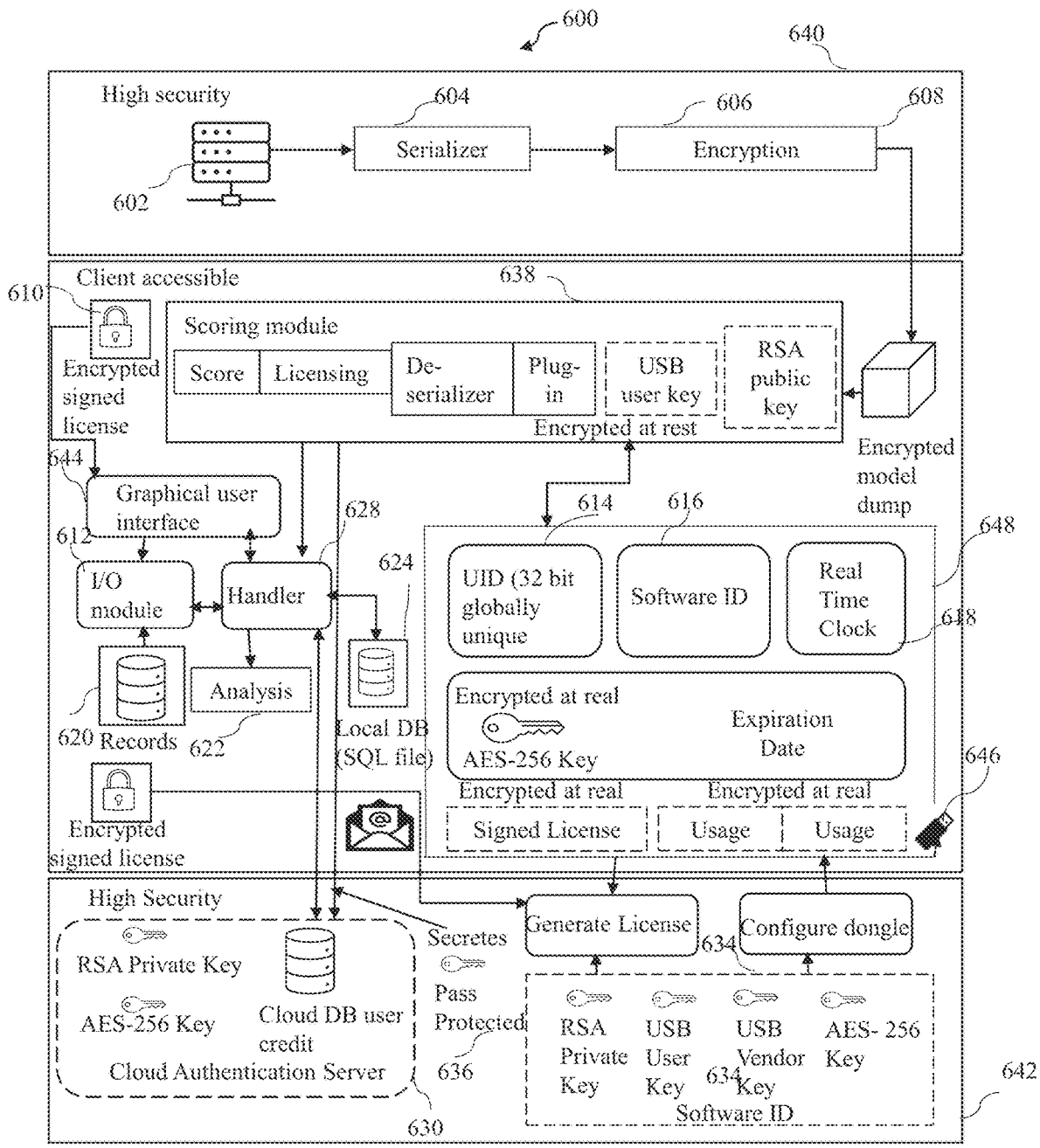
FIG. 6 is a block diagram representing architectural layout of the computer-implemented system for diagnosing sleep disorders of FIG. 1 in accordance with an embodiment of the present disclosure.

FIG. 6 is a block diagram representing architectural layout of the computer-implemented system for diagnosing sleep disorders of FIG. 1 in accordance with an embodiment of the present disclosure. In one embodiment, the computer-implemented system is divided into two distinct areas-one being client or user accessible and other being accessible to analysis software provider designated as high security 640, 642. The GUI module 644, I/O module 612, scoring module 638, the licensing module 402, the handler module 628 constitute the analysis software installed on the user workstation. For security reasons, the licensing module 402 is implemented inside the scoring module 638. The USB licensing dongle 648 or HSM 646 if being utilized is also available on the client side. The raw data records the analysis or scores 622, the usage data stored in a local database 624 and the encrypted AI model dump are also installed or are available on the user workstation. To enforce the tokenization of analytics in the offline mode, the HSM 646 is utilized. Only when a HSM with specified architecture and a designated software ID 616 is connected to the workstation, the analysis software will be authorized to operate. The HSM 646 therefore serves as an authorization key as well as a repository to store the license and credits. Communication with the HSM 646 is secure. In an optimal implementation, traditional security protocols like SSL/TLS is used to secure the communications between the client and cloud servers. Security between the client and HSM 646 is enforced using a secret key. In the preferred embodiment, the secret key is in the form of a USB user and vendor key 634. The USB user key allow full access to the dongle except for change in the software identification number (ID), RTC time and expiration date. To be able to set or update these, both the USB user and vendor key are required. It must be noted that to set the dongle or update these values the dongle must be physically present on the high security side. The USB vendor key therefore is stored on the high security side. Each HSM 646 has a globally unique id (UUID) and the RTC 618 to keep time independent of the workstation. The license is digitally signed using asymmetric cryptography. In the preferred embodiment, 3072-bit RSA algorithm is used. This comprises of an RSA private key and an RSA public key. The private key is only available on the high security section. While the public key is internally embedded within the scoring module. In a cloud authentication mode, the license, authorization, and credit accounting are carried out by the cloud authentication server 630. As the server is outside the reach of the client, it is trivial to secure the server using standard server security protocols. This however does not prevent tampering of data as it enters the client accessible side. This is especially important for communication between the scoring module and the cloud authentication server. For the HSM 646, as the communication is at a hardware level, tampering the data is still considerably complex. To prevent tampering of tokenization protocols in the cloud authentication mode, an additional handshake-based protocol is implemented. In this protocol, each communication initiated by the scoring module, includes a random handshake sequence. In the preferred embodiment, this is a base 64 encoded 256-bit random sequence. When the cloud server 630 responds to this communication, the original handshake sequence is included in the response. Additionally, the response is signed by the RSA private key. The scoring module ensures that the response includes the same handshake sequence it sent, and the signature is valid using the public RSA key. Any tampering of data would cause at least one of the tests to fail.

In one embodiment, the lack of online access to the client when operating in HSM based authorization, presents a challenge in updating the credits or license. While this can be done by physically sending the dongle back to the high security area or sending a new dongle with updated credits and license, both these methods are time consuming, costly and would disrupt the workflow. To address this a over the air (OTA) update protocol is disclosed. On the high security side, a new license can be generated. This license is designated only for a particular HSM 646 based on its UID 614. The license is first signed by the RSA private key then encrypted using the HSM UID. For encryption, the UID is combined with a secret salt and hashed to generate a 256-bit key. AES-256 is then used to encrypt the license. This encrypted and signed license can then be digitally sent to the client. The communication channel could be email or messaging. The license is then imported through the GUI which passes it to the scoring module through the handler 628. The scoring module verifies that the license has not been tampered with using the RSA public key and ensures that it is meant for the HSM connected to the client by decrypting it using the HSM UID. If it succeeds, it then installs the new license into the dongle 648. It must be noted that the software ID, RTC time and expiration date cannot be changed using the OTA protocol. The secrete key 636 is protected and hashed using Bcrypt to create AES key 636.

All machine learning models 602 associated with the scoring module 638 are first serialized 604 then encrypted 606 using an Advanced Encryption Standard (AES)-256 key 608 to generate 632 an encrypted model dump. In the preferred embodiment, the encrypted models are serialized into the Open Neural Network Exchange (ONNX) format. The key 608 to decrypt the models is made available through the HSM 646 or through the cloud authentication server. To protect the source code involved in the algorithms in the scoring module 638, the scoring module 638 is compiled to machine code. In the preferred embodiment, the scoring module 638 as well as analytics are developed in Python. The code is first transpiled to C language and then compiled to a shared object (SO) on Mac and Linux and a dynamic link library (DLL) on windows. To protect the encryption keys from leaking, all keys are encrypted in rest and never stored in plain text. This is important as plain text keys remain as plain text even after compilation of the code. The scoring module 638 can be updated or extend later appropriately updating the NDF format specification, the montage specification and introducing the new or updated analysis within the scoring module. A plugin system within the scoring module 638 provides an interface to carry out the update.

Figure 7:
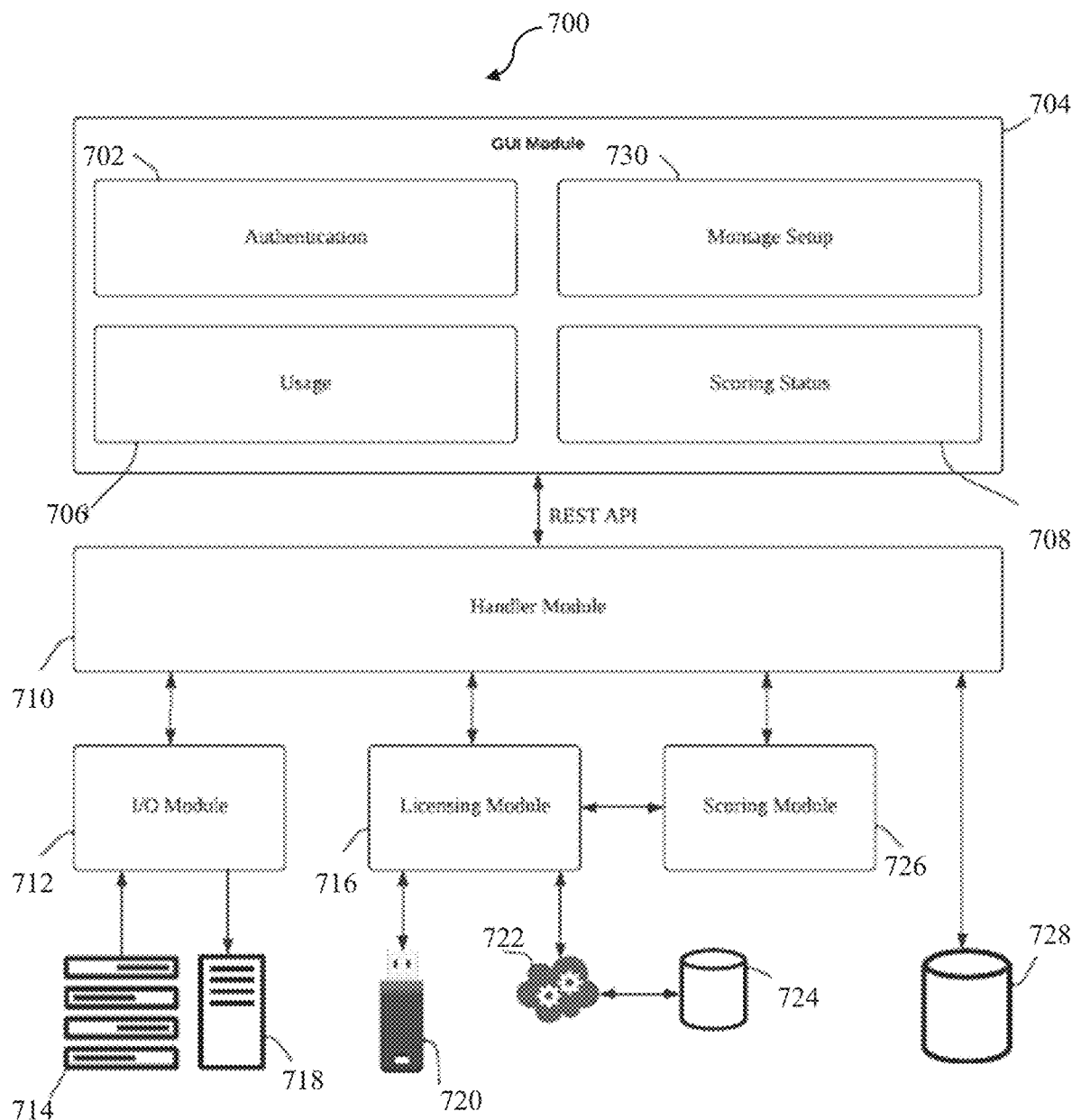
FIG. 7 is a block diagram representing an exemplary embodiment of architectural layout of the computer-implemented system for diagnosing sleep disorders of FIG. 1 in accordance with an embodiment of the present disclosure.

FIG. 7 is a block diagram representing an exemplary embodiment of architectural layout of the computer-implemented system for diagnosing sleep disorders of FIG. 1 in accordance with an embodiment of the present disclosure. In one embodiment, the architecture includes a GUI module 704, the I/O module 712, licensing module 716 and the scoring module 726. In the preferred embodiment, the computer implemented system 700 is deployed as an installable software. To enforce software development best practices of separation of concerns, a model-view-controller paradigm is adopted. Specifically, the GUI implements the visual elements of the computer implemented system 700 which communicates with a controller which is implemented as the handler module 710. This includes authentication 702, montage setup 730, logs of usage 706 and the scoring status 708. The I/O module 712, licensing module 716 and scoring module 726 are operatively coupled with the handler module 710. The model or data resides on the workstation in the form of records 714 for analysis 718. The HSM 720 to store license and authorization locally, a local database 728 to store the montage specifications and usage logs 722 and cloud database 724 to store license and user details. In the preferred embodiment, the GUI is implemented in the electron framework, the handler is implemented as a REST based local server developed in Python/Django framework. As the licensing module implements the tokenization and the scoring module includes proprietary IP, additional protocols and methods are applied to enforce the tokenization and protect the sensitive IP.

Figure 8:
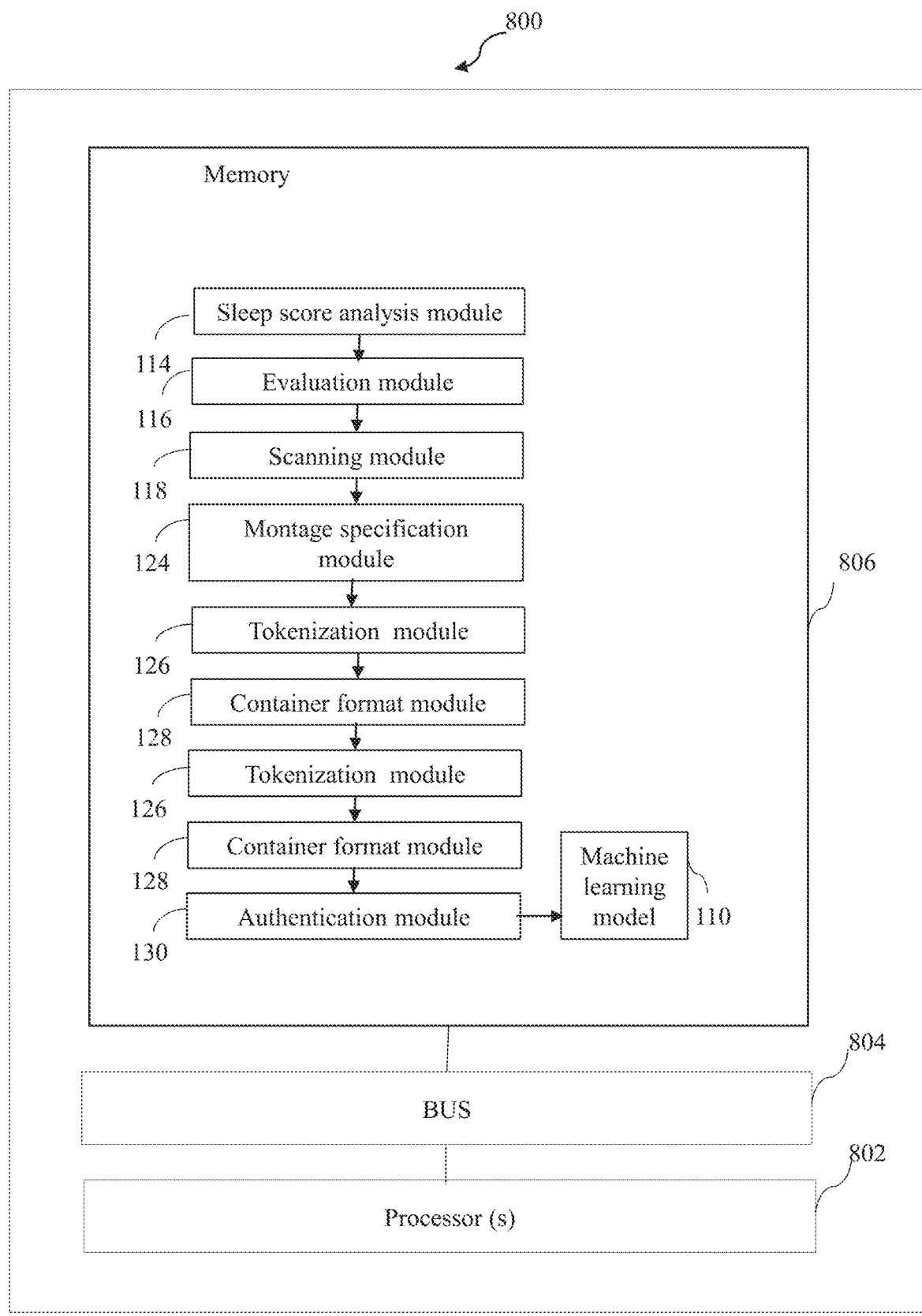
FIG. 8 is a block diagram of a computer or a server for the computer-implemented system for diagnosing sleep disorders in accordance with an embodiment of the present disclosure.

FIG. 8 is a block diagram of a computer or a server for the computer-implemented system for diagnosing sleep disorders in accordance with an embodiment of the present disclosure. The server includes a processor(s) 802, and memory 802 operatively coupled to the bus 804.

The processor(s) 802 as used herein, means any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a digital signal processor, or any other type of processing circuit, or a combination thereof.

The bus 804 as used herein refers to be internal memory channels or computer network that is used to connect computer components and transfer data between them. The bus 804 includes a serial bus or a parallel bus, wherein the serial bus transmits data in a bit-serial format and the parallel bus transmits data across multiple wires. The bus 804 as used herein, may include but not limited to, a system bus, an internal bus, an external bus, an expansion bus, a frontside bus, a backside bus, and the like.

The memory 806 includes a plurality of subsystems and a plurality of modules stored in the form of an executable program which instructs the processor to the computer-implemented system illustrated in FIG. 1. The memory 806 is substantially similar for the ecosystem for procuring and managing marketplace services for a business of FIG. 1. The memory 806 has submodules:

The sleep score analysis module 114 is configured as a series of analytical blocks for automatically processing a data format to produce a standardized format of a sleep score. The sleep score analysis module 114 uses the license and a plurality of montage specifications.

The evaluation module 116 is operatively connected to the sleep score analysis module 114 and configured to review and edit the sleep score for quality control by a physician 120.

The scanning module 118 is operatively connected to the sleep score analysis module 114 and configured to scan the record of the sleep score and store within a repository 140 on a workstation 138 to extract names of a plurality of channels and display the extracted channels to the physician 120. The plurality of channels comprises a plurality of signals generated from physical part of a patient 122.

The scanning module 118 is configured to enable the physician 120 to align the plurality of channels with corresponding channel names present in recordings. The scanning module 118 is also configured to enable the physician 120 to input a criteria for an automated scoring process. The criteria includes a format for saving a sleep score, a predetermined demographic details, and a plurality of guidelines required for sleep scoring.

The montage specification module 124 is operatively coupled to the scanning module 118 and the sleep score analysis module 114. The montage specification module 124 is configured to store the plurality of montage specifications as a predefined notation dictionary.

The tokenization module 126 is operatively connected with the montage specification module 124. The tokenization module 126 is configured to grant a pre-determined a plurality of distributed credits in at least one of the analytical blocks, to a user, each block of credit comprises an expiration date. The tokenization module 126 is also configured to provide a plurality of scoring methods for providing an analysis service, each service is designed for a specific scoring aspect and a predefined types of recordings. Further, the tokenization module 126 is configured to associate the analysis service with a cost multiplier, wherein the analysis service is disabled by assigning a negative cost multiplier. Furthermore, the tokenization module 126 is configured to register the tokenization as a tokenization license including a credit block, the expiration date, a license type, and the cost multiplier table. The tokenization license is stored in a cryptographic storage device connected directly to the workstation or on a cloud authentication server. Furthermore, the tokenization module 126 is configured to allow a key-based authentication for offline setting and enforce the tokenization in an offline setting, the tokenization licenses and a credit accounting and are carried out in a hardware security module with a real-time clock and a unique identifier. Furthermore, the tokenization module 126 is configured to sign the license and a communication between the sleep scoring analysis module via an asymmetric key cryptography on the workstation and the cloud authentication server. Furthermore, the tokenization module 126 is configured to update the license using over-the-air mechanism, wherein the updating is irrespective of the workstation connection with Internet.

The container format module 128 is operatively connected with the tokenization module 128 and configured for handling physiological sleep data, wherein a container format module 128 comprises a signature, a header, and a payload. The signature includes a predetermined bytes to inform an operating system about the container format and a byte indicating payload compression. The header is of a fixed length and carries a string representing a dictionary that includes version, revision, record duration, start date and time for the recording, unique identifier, and a plurality of field listing keys, wherein, the plurality of field listing keys is defined in header is present in payload.

The authentication module 130 is operatively connected with montage specification module 124. The authentication module 130 is configured to protect a plurality of machine learning models by using a symmetric encryption method. The authentication module 130 is configured to compile a code into machine code to protect a source code. Further, the authentication module 130 is configured to serialize the plurality of machine learning models, encrypt the plurality of machine learning models using a key and deploy into an analytics application. The analytics application requests an encryption key to decrypt and deserialize the machine learning models for performing analysis.

Computer memory elements may include any suitable memory device(s) for storing data and executable program, such as read-only memory, random access memory, erasable programmable read-only memory, electrically erasable programmable read-only memory, hard drive, removable media drive for handling memory cards and the like. Embodiments of the present subject matter may be implemented in conjunction with program modules, including functions, procedures, data structures, and application programs, for performing tasks, or defining abstract data types or low-level hardware contexts. An executable program stored on any of the above-mentioned storage media may be executable by the processor(s) 802.

Figure 9A:
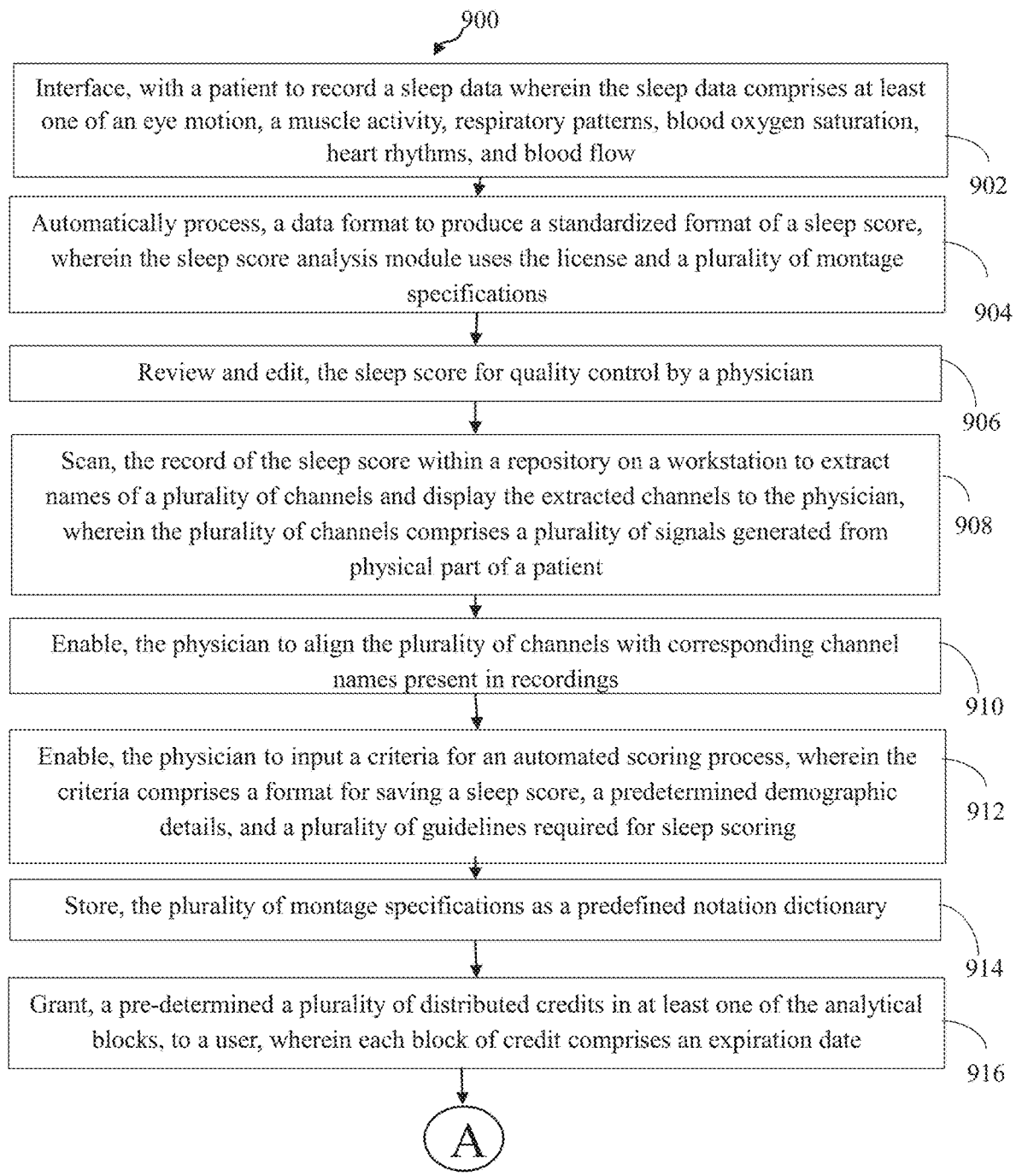
FIG. 9a is a flow chart representing steps involved in of a method for for diagnosing sleep disorders in accordance with an embodiment of the present disclosure.
Figure 9B:
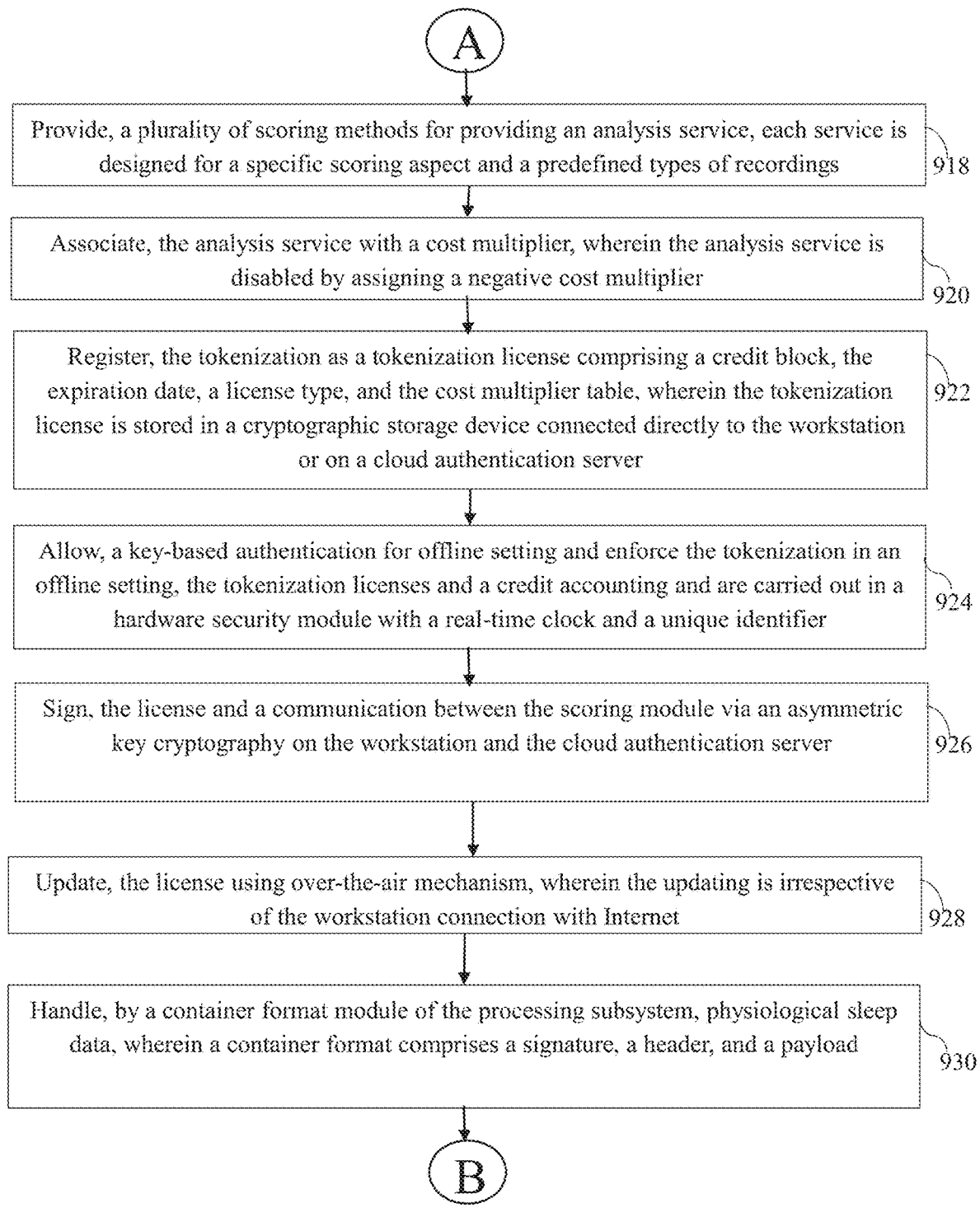
FIG. 9b illustrates continued steps involved in of a method for for diagnosing sleep disorders of FIG. 9a in accordance with an embodiment of the present disclosure.
Figure 9C:
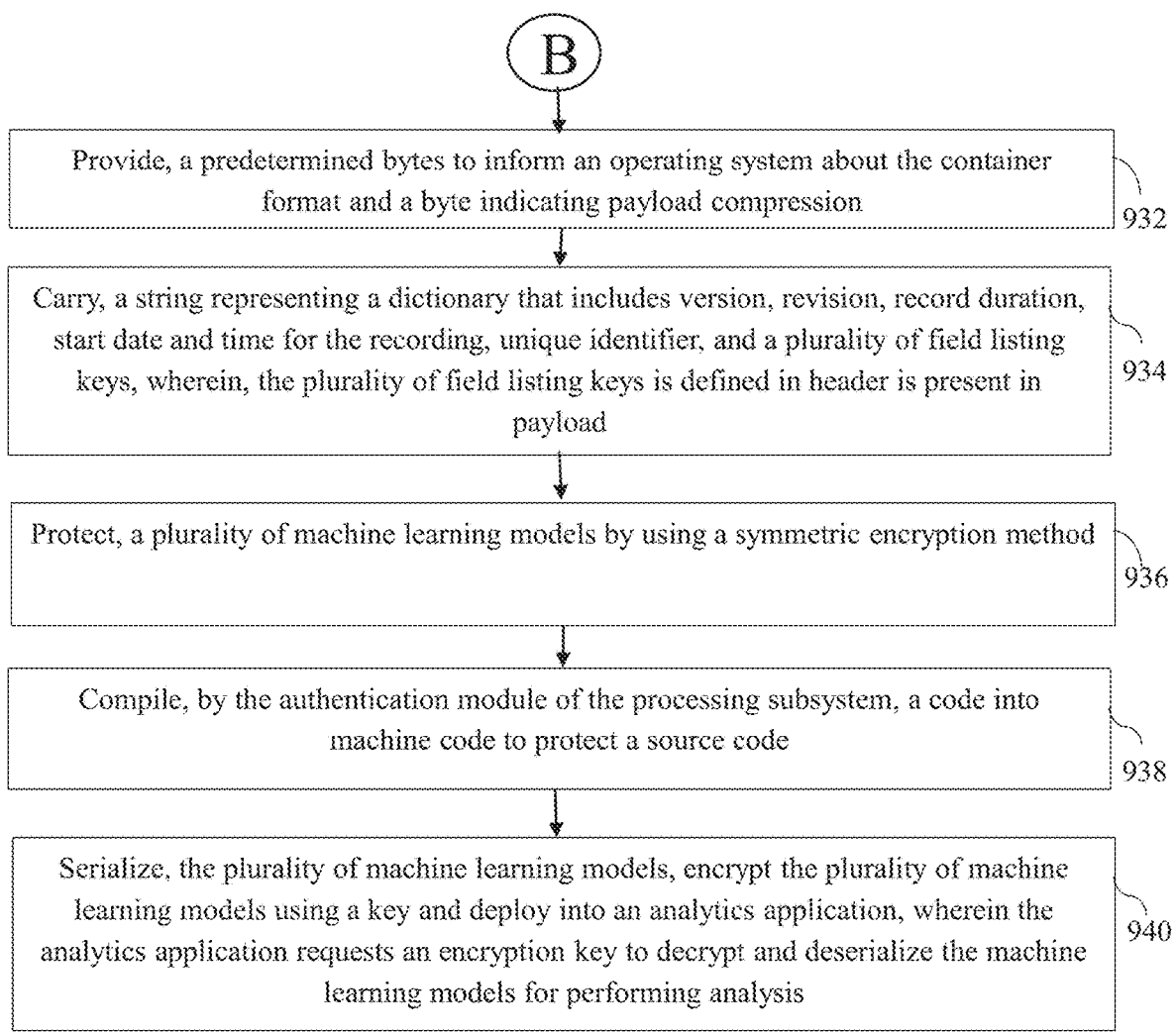
FIG. 9c illustrates continued steps involved in of a method for for diagnosing sleep disorders of FIG. 9b in accordance with an embodiment of the present disclosure.

FIG. 9a is a flow chart representing steps involved in of a method for diagnosing sleep disorders in accordance with an embodiment of the present disclosure, FIG. 9b illustrates continued steps involved in of a method for diagnosing sleep disorders of FIG. 9a in accordance with an embodiment of the present disclosure and FIG. 9c illustrates continued steps involved in of a method for diagnosing sleep disorders of FIG. 9b in accordance with an embodiment of the present disclosure.

The method 900 includes interfacing, by a polysomnography recording device, with a patient to record a sleep data wherein the sleep data comprises at least one of an eye motion, a muscle activity, respiratory patterns, blood oxygen saturation, heart rhythms, and blood flow in step 902.

The method 900 also includes automatically processing, by a sleep score analysis module of a processing subsystem, a data format to produce a standardized format of a sleep score, wherein the sleep score analysis module uses the license and a plurality of montage specifications in step 904.

Further, the method 900 includes reviewing and editing, by an evaluation module of the processing subsystem, the sleep score for quality control by a physician in step 906.

Furthermore, the method 900 includes scanning, by a scanning module of the processing subsystem, the record of the sleep score within a repository on a workstation to extract names of a plurality of channels and display the extracted channels to the physician, wherein the plurality of channels comprises a plurality of signals generated from physical part of a patient in step 908.

Furthermore, the method 900 includes enabling, by the scanning module of the processing subsystem, the physician to align the plurality of channels with corresponding channel names present in recordings in step 910.

Furthermore, the method 900 includes enabling, by the scanning module of the processing subsystem, the physician to input a criteria for an automated scoring process, wherein the criteria comprises a format for saving a sleep score, a predetermined demographic details, and a plurality of guidelines required for sleep scoring in step 912.

Furthermore, the method 900 includes storing, by a montage specification module of the processing subsystem, the plurality of montage specifications as a predefined notation dictionary in step 914.

Furthermore, the method 900 includes granting, by a tokenization module of the processing subsystem, a predetermined a plurality of distributed credits in at least one of the analytical blocks, to a user, wherein each block of credit includes an expiration date in step 916.

Furthermore, the method 900 includes providing, by tokenization module of the processing subsystem, a plurality of scoring methods for providing an analysis service, each service is designed for a specific scoring aspect and a predefined types of recordings in step 918.

Furthermore, the method 900 includes associating, by tokenization module of the processing subsystem, the analysis service with a cost multiplier, wherein the analysis service is disabled by assigning a negative cost multiplier in step 920.

Furthermore, the method 900 includes registering, by tokenization module of the processing subsystem, the tokenization as a tokenization license comprising a credit block, the expiration date, a license type, and the cost multiplier table, the tokenization license is stored in a cryptographic storage device connected directly to the workstation or on a cloud authentication server in step 922.

Furthermore, the method 900 includes allowing, by tokenization module of the processing subsystem, a key-based authentication for offline setting and enforce the tokenization in an offline setting, the tokenization licenses and a credit accounting and are carried out in a hardware security module with a real-time clock and a unique identifier in step 924.

Furthermore, the method 900 includes signing, by tokenization module of the processing subsystem, the license, and a communication between the sleep scoring analysis via an asymmetric key cryptography on the workstation and the cloud authentication server in step 926.

Furthermore, the method includes 900 updating, by tokenization module of the processing subsystem, the license using over-the-air mechanism, wherein the updating is irrespective of the workstation connection with Internet in step 928.

Furthermore, the method includes handling, by a container format module of the processing subsystem, physiological sleep data, wherein a container format comprises a signature, a header, and a payload in step 930.

Furthermore, the method 900 includes providing, by the container format module of the processing subsystem, a predetermined bytes to inform an operating system about the container format and a byte indicating payload compression in step 932.

Furthermore, the method 900 includes carrying, by the header of the by the container format module of the processing subsystem, a string representing a dictionary that includes version, revision, record duration, start date and time for the recording, unique identifier, and a plurality of field listing keys, wherein, the plurality of field listing keys is defined in header is present in payload in step 934.

Furthermore, the method 900 includes protecting, by an authentication module of the processing subsystem, a plurality of machine learning models by using a symmetric encryption method in step 936.

Furthermore, the method 900 includes compiling, by the authentication module of the processing subsystem, a code into machine code to protect a source code in step 938.

Furthermore, the method 900 includes serializing, by the authentication module of the processing subsystem, the plurality of machine learning models, encrypt the plurality of machine learning models using a key and deploy into an analytics application, wherein the analytics application requests an encryption key to decrypt and deserialize the machine learning models for performing analysis in step 940.

Various embodiments of the present disclosure provide an automatic computer implemented system for diagnosing sleep disorders. The computer implemented system disclosed in the present disclosure provides a time-efficient system by avoiding manual labour, variability, and potential bias across different raters. The computer implemented system disclosed in the present disclosure provides a cost-effective system as it does not require specialized training and expertise, which may not be readily available in all clinical settings.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, the order of processes described herein may be changed and is not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

We claim:

1. A computer-implemented system for diagnosing sleep disorders comprising:
   a hardware processor;
   a polysomnography recording device is configured to interface with a patient to record a sleep data wherein the sleep data comprises at least one of an eye motion, a muscle activity, respiratory patterns, blood oxygen saturation, heart rhythms, and blood flow;
   a memory coupled to the hardware processor and the polysomnography recording device, wherein the memory comprises a set of instructions in the form of a processing subsystem, configured to be executed by the hardware processor, wherein the processing subsystem is hosted on a server, and configured to execute on a network to control bidirectional communications among a plurality of modules wherein the plurality of modules comprises:
   a sleep score analysis module configured as a series of analytical blocks for automatically processing a data format to produce a standardized format of a sleep score, wherein the sleep score analysis module uses a license and a plurality of montage specifications;
   an evaluation module operatively connected to the sleep score analysis module and configured to review and edit the sleep score for quality control by a physician;
   a scanning module operatively connected to the sleep score analysis module and configured to scan the record of the sleep score within a repository on a workstation to extract names of a plurality of channels and display the extracted channels to the physician,
   wherein the plurality of channels comprises a plurality of signals generated from physical part of a patient, wherein, the scanning module enables the physician to align the plurality of channels with corresponding channel names present in recordings, and
   wherein, the scanning module enables the physician to input a criteria for an automated scoring process detect a sleep disorder, wherein the criteria comprises a format for saving a sleep score, a predetermined demographic details, and a plurality of guidelines required for sleep scoring;
   a montage specification module operatively coupled to the scanning module and the sleep score analysis module, wherein the montage specification module is configured to store the plurality of montage specifications as a predefined notation dictionary;
   a tokenization module operatively connected with the montage specification module, wherein the tokenization module is configured to:
   grant a pre-determined a plurality of distributed credits in at least one of the analytical blocks, to a user, wherein each block of credit comprises an expiration date;
   provide a plurality of scoring methods for providing an analysis service, each service is designed for a specific scoring aspect and a predefined types of recordings;
   associate the analysis service with a cost multiplier, wherein the analysis service is disabled by assigning a negative cost multiplier;
   register the tokenization as a tokenization license comprising a credit block, the expiration date, a license type, and the cost multiplier table, wherein the tokenization license is stored in a cryptographic storage device connected directly to the workstation or on a cloud authentication server, allow a key-based authentication for offline setting and enforce the tokenization in an offline setting, the tokenization licenses and a credit accounting and are carried out in a hardware security module with a real-time clock and a unique identifier;

sign the license and a communication between the sleep scoring analysis via an asymmetric key cryptography on the workstation and the cloud authentication server;

update the license using over-the-air mechanism, wherein the updating is irrespective of the workstation connection with Internet;

a container format module operatively connected with the tokenization module and configured for handling physiological sleep data, wherein a container format comprises a signature, a header, and a payload, wherein, the signature comprises a predetermined bytes to inform an operating system about the container format and a byte indicating payload compression, and wherein, the header is of fixed length and carries a string representing a dictionary that includes version, revision, record duration, start date and time for the recording, unique identifier, and a plurality of field listing keys, wherein, the plurality of field listing keys is defined in header is present in payload; and an authentication module operatively connected with montage specification module, wherein the authentication module is configured to:

protect a plurality of machine learning models by using a symmetric encryption method;

compile a code into machine code to protect a source code;

and serialize the plurality of machine learning models, encrypt the plurality of machine learning models using a key and deploy into an analytics application, wherein the analytics application requests an encryption key to decrypt and deserialize the machine learning models for performing analysis.

2. The computer-implemented system according to claim 1, further comprising a display module operatively coupled to a sleep score analysis module wherein the display module is configured to display a report related to the sleep score upon analyzing the sleep data and integrates the report with an electronic recording unit to forward the report to a physician.

3. The computer-implemented system according to claim 1, wherein the sleep score analysis module categorizes the sleep score as a plurality of phases of sleep, events corresponding to annotations demarcating important events associated with the sleep record, biomarkers to capture measurements from the sleep record and a time series depicting a chronological representation of measurements over the duration of the recording.

4. The computer-implemented system according to claim 1, wherein the cryptographic storage device is a universal serial bus dongle.

5. The computer-implemented system according to claim 1, wherein the license is updated offline by importing a cryptographically signed and encrypted file.

6. The computer-implemented system according to claim 1, comprises a plurality of recording devices, wherein each device is having a unique set of channels, technical specifications, and a noise profile to standardize a raw data, wherein the raw data is an unstructured data.

7. The computer-implemented system according to claim 1, comprises an interface module designed to standardize the raw data and an output score, wherein the output score is the output of the sleep score.

8. The computer-implemented system according to claim 1, wherein the plurality of machine learning models are serialized into an open neural network exchange format.

9. The computer-implemented system according to claim 1, wherein analytical blocks processes Neurobit Data Format.

10. A method for analyzing sleep for diagnosing sleep disorder comprising:

interfacing, by a polysomnography recording device, with a patient to record a sleep data wherein the sleep data comprises at least one of an eye motion, a muscle activity, respiratory patterns, blood oxygen saturation, heart rhythms, and blood flow;

automatically processing, by a sleep score analysis module of a processing subsystem, a data format to produce a standardized format of a sleep score, wherein the sleep score analysis module uses a license and a plurality of montage specifications;

reviewing and editing, by an evaluation module of the processing subsystem, the sleep score for quality control by a physician;

scanning, by a scanning module of the processing subsystem, the record of the sleep score within a repository on a workstation to extract names of a plurality of channels and display the extracted channels to the physician, wherein the plurality of channels comprises a plurality of signals generated from physical part of a patient;

enabling, by the scanning module of the processing subsystem, the physician to align the plurality of channels with corresponding channel names present in recordings;

enabling, by the scanning module of the processing subsystem, the physician to input a criteria for an automated scoring process and detect a sleep disorder, wherein the criteria comprises a format for saving a sleep score, a predetermined demographic details, and a plurality of guidelines required for sleep scoring;

storing, by a montage specification module of the processing subsystem, the plurality of montage specifications as a predefined notation dictionary;

granting, by a tokenization module of the processing subsystem, a pre-deterermined a plurality of distributed credits in at least one of the analytical blocks, to a user, wherein each block of credit comprises an expiration date; providing, by tokenization module of the processing subsystem, a plurality of scoring methods for providing an analysis service, each service is designed for a specific scoring aspect and a predefined types of recordings;

associating, by tokenization module of the processing subsystem, the analysis service with a cost multiplier, wherein the analysis service is disabled by assigning a negative cost multiplier;

registering, by tokenization module of the processing subsystem, the tokenization as a tokenization license comprising a credit block, the expiration date, a license type, and the cost multiplier table, wherein the tokenization license is stored in a cryptographic storage device connected directly to the workstation or on a cloud authentication server;

allowing, by tokenization module of the processing subsystem, a key-based authentication for offline setting and enforce the tokenization in an offline setting, the tokenization licenses and a credit accounting and are carried out in a hardware security module with a real-time clock and a unique identifier;

signing, by tokenization module of the processing subsystem, the license, and a communication between the sleep scoring analysis via an asymmetric key cryptography on the workstation and the cloud authentication server;

updating, by tokenization module of the processing subsystem, the license using over-the-air mechanism, wherein the updating is irrespective of the workstation connection with Internet;

handling, by a container format module of the processing subsystem, physiological sleep data, wherein a container format comprises a signature, a header, and a payload;

providing, by the container format module of the processing subsystem, a predetermined bytes to inform an operating system about the container format and a byte indicating payload compression;

carrying, by the header of the by the container format module of the processing subsystem, a string representing a dictionary that includes version, revision, record duration, start date and time for the recording, unique identifier, and a plurality of field listing keys, wherein, the plurality of field listing keys is defined in header is present in payload;

protecting, by an authentication module of the processing subsystem, a plurality of machine learning models by using a symmetric encryption method;

compiling, by the authentication module of the processing subsystem, a code into machine code to protect a source code; and serializing, by the authentication module of the processing subsystem, the plurality of machine learning models, encrypt the plurality of machine learning models using a key and deploy into an analytics application, wherein the analytics application requests an encryption key to decrypt and deserialize the machine learning models for performing analysis.

11. The method according to claim 10, comprises providing a key based authentication through a user-friendly graphical user interface integrated within the analysis application.

12. The method according to claim 10, comprises determining, the plurality of channels and the subsequent feature extraction and signal conditioning processes.

13. The method according to claim 10, comprises authenticating, the plurality of machine learning model using an advanced encryption standard method.

14. The method according to claim 10, comprises transpiling, a plurality of machine learning model to a predefined language and compiling the transpiled machine learning model to the machine code in the form of a shared object in a first predefined platform and dynamic link library a second predefined platforms.

15. The method according to claim 10, comprises utilizing, a single credit for allowing the user to assess one sleep record and dictating though the definition of a record within the license.

16. The method according to claim 10, comprises implementing, a plurality of visual elements for communicating with a controller.

17. The method according to claim 10, comprises recording, physiological signals in in-lab and home settings across a clinically approved device by using a polysomnography device.

18. The method according to claim 10, comprises allowing, the physician to review and edit the automatically generated sleep scores for obtaining accurate output.

19. The method according to claim 10, comprises:
conducting, feature extraction and signal conditioning processes based on the requirements of the sleep scoring analysis;

selecting, selection menu to select the appropriate credit management and authentication; and transmitting, the encrypted license to the user through a digital communication methods.

20. A non-transitory computer-readable medium storing a computer program that, when executed by a processor, causes the processor to perform a method for analyzing sleep for diagnosing sleep disorder, wherein the method comprises:

interfacing, by a polysomnography recording device, with a patient to record a sleep data wherein the sleep data comprises at least one of an eye motion, a muscle activity, respiratory patterns, blood oxygen saturation, heart rhythms, and blood flow;

automatically processing, by a sleep score analysis module of a processing subsystem, a data format to produce a standardized format of a sleep score, wherein the sleep score analysis module uses a license and a plurality of montage specifications;

reviewing and editing, by an evaluation module of the processing subsystem, the sleep score for quality control by a physician;

scanning, by a scanning module of the processing subsystem, the record of the sleep score within a repository on a workstation to extract names of a plurality of channels and display the extracted channels to the physician, wherein the plurality of channels comprises a plurality of signals generated from physical part of a patient;

enabling, by the scanning module of the processing subsystem, the physician to align the plurality of channels with corresponding channel names present in recordings;

enabling, by the scanning module of the processing subsystem, the physician to input a criteria for an automated scoring process detect a sleep disorder, wherein the criteria comprises a format for saving a sleep score, a predetermined demographic details, and a plurality of guidelines required for sleep scoring;

storing, by a montage specification module of the processing subsystem, the plurality of montage specifications as a predefined notation dictionary;

granting, by a tokenization module of the processing subsystem, a pre-determined a plurality of distributed credits in at least one of the analytical blocks, to a user, wherein each block of credit comprises an expiration date;

providing, by tokenization module of the processing subsystem, a plurality of scoring methods for providing an analysis service, each service is designed for a specific scoring aspect and a predefined types of recordings;

associating, by tokenization module of the processing subsystem, the analysis service with a cost multiplier, wherein the analysis service is disabled by assigning a negative cost multiplier; registering, by tokenization module of the processing subsystem, the tokenization as a tokenization license comprising a credit block, the expiration date, a license type, and the cost multiplier table, wherein the tokenization license is stored in a cryptographic storage device connected directly to the Workstation or on a cloud authentication server;

allowing, by tokenization module of the processing subsystem, a key-based authentication for offline setting and enforce the tokenization in an offline setting, the tokenization licenses and a credit accounting and are carried out in a hardware security module with a real-time clock and a unique identifier;

signing, by tokenization module of the processing subsystem, the license, and a communication between the sleep scoring analysis via an asymmetric key cryptography on the workstation and the cloud authentication server;

updating, by tokenization module of the processing subsystem, the license using over-the-air mechanism, wherein the updating is irrespective of the workstation connection with Internet;

handling, by a container format module of the processing subsystem, physiological sleep data, wherein a container format comprises a signature, a header, and a payload;

providing, by the container format module of the processing subsystem, a predetermined bytes to inform an operating system about the container format and a byte indicating payload compression;

carrying, by the header of the by the container format module of the processing subsystem, a string representing a dictionary that includes version, revision, record duration, start date and time for the recording, unique identifier, and a plurality of field listing keys, wherein, the plurality of field listing keys is defined in header is present in payload;

protecting, by an authentication module of the processing subsystem, a plurality of machine learning models by using a symmetric encryption method;

compiling, by the authentication module of the processing subsystem, a code into machine code to protect a source code; and serializing, by the authentication module of the processing subsystem, the plurality of machine learning models, encrypt the plurality of machine learning models using a key and deploy into an analytics application, wherein the analytics application requests an encryption key to decrypt and deserialize the machine learning models for performing analysis.

* * * * *